United States Patent [19]

Huybrechts

[11] Patent Number: 5,548,848
[45] Date of Patent: Aug. 27, 1996

[54] MOULDABLE COMPOSITION AND METHOD OF MAKING IT

[76] Inventor: Robert Huybrechts, 18484 Keele St. North RR#2, Newmarket, Ontario, Canada, L3Y 4V9

[21] Appl. No.: 458,249

[22] Filed: Jun. 2, 1995

Related U.S. Application Data

[60] Division of Ser. No. 271,993, Jul. 8, 1994, Pat. No. 5,431,563, which is a continuation-in-part of Ser. No. 992,752, Dec. 18, 1992, abandoned.

[51] Int. Cl.⁶ .................. A42B 3/00; A43B 13/38
[52] U.S. Cl. .................. 2/425; 16/DIG. 12; 36/43; 433/48; 128/862; 523/109
[58] Field of Search .................. 433/48; 128/862; 523/109; 525/309; 524/458, 560

[56] References Cited

U.S. PATENT DOCUMENTS

| | | | |
|---|---|---|---|
| 4,161,065 | 7/1979 | Gigante | 32/2 |
| 4,568,280 | 2/1986 | Ahlin | 433/6 |
| 4,759,798 | 7/1988 | von Nostitz | 106/35 |
| 4,791,184 | 12/1988 | Nagai et al. | 525/305 |
| 4,946,901 | 8/1990 | Lechner et al. | 525/305 |
| 5,051,482 | 9/1991 | Topic | 525/309 |
| 5,055,529 | 10/1991 | Kishida et al. | 525/309 |
| 5,182,332 | 1/1993 | Yamamato et al. | 525/305 |
| 5,431,563 | 7/1995 | Huybrechts | 433/48 |

*Primary Examiner*—Vasu S. Jagannathan

[57] ABSTRACT

A thermoplastic article formed of a composition for customizable moulding parts of devices such as hand grips or sports equipment or orthopaedic equipment comprises a composition which is set below 37° C. and is conformably mouldable between about 50° C. and 95° C. The article can be moulded, used, and re-moulded and re-used, repeatedly. Such a composition may be an acrylate polymer, possibly a methacrylate polymer. The acrylate polymer may soften or become liquid in the range of 50° C. to 95° C. and may be mixed with another such polymer which is set at that temperature range so that a pasty mouldable mass is formed, for example by warming in warm water. The invention includes a method of forming the composition.

7 Claims, 1 Drawing Sheet

MOULDABLE COMPOSITION AND METHOD OF MAKING IT

FIELD OF THE INVENTION

The invention relates to a thermoplastic conformably re-mouldable article and to a device incorporating such an article and in particular, to an orthopaedic support body which is repeatedly re-mouldable to conform to portions of the body, and a method of forming a moulded support article. This application is a divisional application of U.S. patent application Ser. No. 08/271,993 filed Jul. 8, 1994 U.S. Pat. No. 5,431,563 entitled Mouldable Composition and Method of Making It, Inventor, Robert Huybrechts, which was a Continuation in Part of U.S. patent application Ser. No. 07/992,752, filed Dec. 18, 1992, abandoned. Title: *Mouldable Composition and Method of Making It,* Inventor Robert Huybrechts.

BACKGROUND OF THE INVENTION

Body support devices or body contact articles, particularly orthopaedic supports are required in numerous circumstances. For example, supports may be required for any portions of the body, for disabled persons. Insoles may be required for shoes, to provide support for the feet. Joint supports may be required for various joints of the body which may have become injured or defective for any reason.

A support may be required for the head or neck, or back. A seat may be required conforming to the shape of an individual.

In addition, in very many cases supports are required for the hand or hands of a person suffering from some kind of disability, A person with no disability at all, may require to have a handle on an article which conforms precisely to the shape of his or her hand. Persons requiring such hand supports may simply require a shaped grip, which conforms precisely to the shape of their hand. Such persons may be craftsman, or may be professionals such as surgeons, or may be sportsmen such as players of various games such as racquet sports, golf and the like or other sportsmen such as fishermen, hunters, and the like any of whom may require an article such as the handle of a golf club, fishing rod, or the stock of a weapon, to be shaped to particularly conform to the hand.

In most cases such a person will not be suffering from any disability, but will merely require a precise match between the shape of the hand grip and their hand. Conversely, persons suffering for example from arthritis of the fingers or other joints may require a hand grip of a peculiar shape, to conform to the somewhat deformed shape of their hand resulting from such a disability and this may have to be re-shaped from time to time.

In the case of certain other sports, shoe, or boot liners or insoles may be required to conform precisely to the shape of the foot. This is particularly required for example in the sport of skiing where the boot is required to fit snugly under the instep and all over the foot. Re-shaping of such boot inserts may be required, as the boots stretch.

Conformable support devices may also be required in many other cases other than orthopaedic situations. Such cases may arise in the case of packaging or containing of precision or scientific instruments, to prevent damage. Other cases may involve the provision of a shaped work support for holding a particular work piece, such as, an item of jewellery for example, while it is being worked upon.

In the past, various different systems have been proposed of more or less considerable complexity and expense. Orthopaedic supports requiring special forming and moulding techniques are of course well known and are manufactured routinely from fast setting plaster materials. In other cases, supports have been shaped from bendable metal sections. In other cases, a complex multi-stage formation process is involved including the steps of making a "plug" in the shape of a limb, or portion of the body or an article, and them forming a support of glass fibre reinforced resin material, with or without padding. In other cases supports such as for example gun stocks are actually carved by hand out of wood, in an effort to as far as possible conform to the hand and body of the user.

Clearly, where such a conformable support device is required, it is desirable if it can be manufactured in a simple one step technique out of low cost materials. Preferably it will be made by direct contact with the portion of the body, or the article, which it is intended to support. In this way any loss of accuracy due to the making of intermediate articles such as plugs, moulds and the like is avoided.

In the particular field of dentistry, it has been known to utilize settable materials for obtaining a form from the mouth or teeth. These settable materials are then used in a multi-stage process for making dentures, or denture supports, or for example making caps for teeth. Such settable materials are of such a nature that generally speaking they do not set completely hard, and are relatively easily distorted out of shape. Consequently, once the form has been taken from the mouth, the materials must then be treated with considerable care.

It is clearly desirable to provide a mouldable body support for any part of the body such as handles, insoles or in the case of spectacles, which may be required to fit the bridge of the nose, or over the ear, which may readily be moulded directly to conform to the shape of the body and will then retain its shape, for as long as is required, but which may be re-moulded and reshaped from time to time and daily if needed in accordance with the needs of the user.

Helmets may also advantageously be provided with liners conform which can be personally moulded to the shape of the skull of the individual.

It is clearly desirable to provide such a re-mouldable body contacting article for other purposes, other than actually supporting parts of the body, whether for orthopaedic purposes or otherwise, and which again will retain its shape, and which may yet be remoulded readily from time to time and daily if needed.

The present invention addresses the above problems.

BRIEF SUMMARY OF THE INVENTION

With a view to solving the various problems and conflicting objectives described above, the invention comprises in a mouldable, settable article forming part of a personally portable device, said article being located on the exterior of said device for contact with the person and being capable of repeated reheating and remoulding for repeated customization to the shape of a portion of the person by a user, a thermoplastic polymerised composition which is set hard in air at ambient temperatures up to about 37° C. and which may be repeatedly rendered conformably mouldable at elevated temperatures of between about 50° C. and 95° C. to repeatedly be moulded to conform to the person, and thereafter remains hard in contact with the person when cooled to body temperature, the thermoplastic polymerised composition containing;

a liquid mixture of a quantity of liquid methyl methacrylate monomer in an amount of about 27 to 76 parts per hundred of said mixture, a quantity of liquid butyl methacrylate monomer in an amount of about 2.5 to 8 parts per hundred of said mixture and a plasticizer mixture in an amount of about 20 to 63 parts per hundred of said mixture; and, a powdered methacrylate polymer and a polymerisation initiator mixed with said liquid mixture in a ratio of about from one part to about two parts by weight of powered methacrylate polymer, to about one part by weight of said liquid mixture, said powdered methacrylate polymer being at least substantially set at temperatures below about 95° C., said liquid mixture and said powdered methacrylate polymer being polymerised, whereby said polymerised composition remains set after polymerisation at temperatures in the region up to about 37° C. and which may be repeatedly rendered substantially manually mouldable at temperatures between about 50° C. and 95° C.

The invention also includes a method of making a thermoplastic composition for use to form a mouldable, settable article capable of customization to shape by a user, comprising mixing a liquid mixture of methacrylate monomer with plasticizer, mixing the liquid mixture with powdered solid methacrylate polymer and polymerization initiator, and polymerizing the methacrylate monomer at elevated temperature to form a composite whereby the resulting composition is set hard at temperatures up to about 37° C. and is repeatedly conformably re-mouldable at temperatures between about 50° C. and 95° C.

The invention includes a re-mouldable, settable hand piece of an article to be held in the hand comprising a base having an approximate generally desired shape and a cover portion for said base, said cover portion comprising a thermoplastic composition which is set at temperatures up to 37° C. and is repeatedly conformably re-mouldable at temperatures in the region of between 50° C. and 95° C.

The hand piece may include a layer of resilient, deformable, flexible material interposed between the base and the cover portion.

The invention also includes other personal articles such as a helmet adapted to fit the head, and an insole adapted to fit the foot, for example.

The various features of novelty which characterize the invention are pointed out with more particularity in the claims annexed to and forming a part of this disclosure. For a better understanding of the invention, its operating advantages and specific objects attained by its use, reference should be had to the accompanying drawings and descriptive matter in which there are illustrated and described preferred embodiments of the invention.

DETAILED DESCRIPTION OF A PREFERRED EMBODIMENTS

As explained above, while the invention is of wide application to many fields, it is explained here partly in the field of its orthopaedic use.

Figure 1:
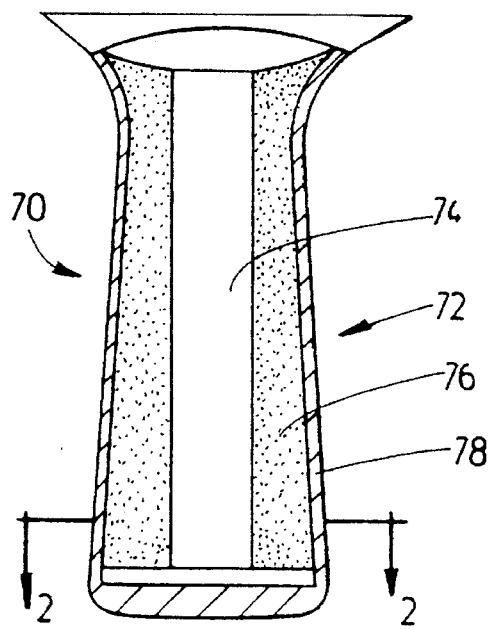
FIG. 1 illustrates the handle of an article, in this case a bat for playing table tennis, showing a conformable and mouldable body in accordance with the invention thereon.
Figure 2:
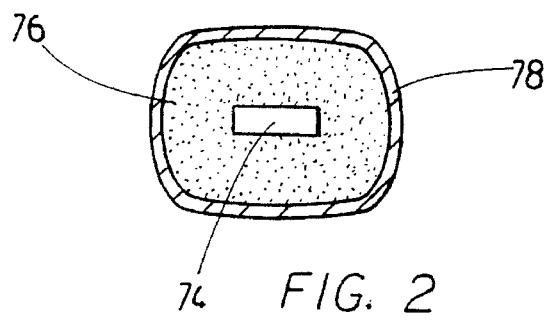
FIG. 2 shows a section of the handle, along line 2—2 of FIG. 1 surrounded by a resilient flexible material, completely wrapped into a layer of thermoplastic material.
Figure 3:
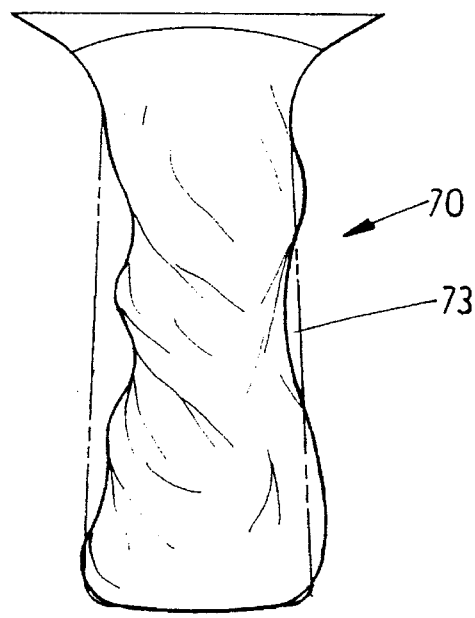
FIG. 3 illustrates the handle of the article of FIG. 1, after being heated and moulded to fit the form of a hand.

FIGS. 1, 2, and 3 illustrate the use of material according to the invention for application to various personal articles, i.e. for custom moulding the hand grip of a piece of sports equipment. Numerous such applications, such as helmets and other protective sportswear, splints, seating, shoe inserts, insoles, and other foot wear, packing material, and the like, are also possible.

It will be appreciated that the general principal may be applied to any or all of these items as will be readily understood from the following description which in this case relates to the moulding of a table tennis bat handle, for the sake of illustration.

A table tennis bat 70 has a handle 72. The handle 72 comprises a central longitudinal core 74 optionally covered by a layer of compressible flexible material 76 such as foamed material. Over the layer of foamed material 76 or, if such material is not present, directly over the core 74, is an outer layer 78 of material according to the invention. The bat handle 72, before customization, may be roughly contoured to the shape of a hand gripping it or it may be substantially non-contoured. To customize the handle it is dipped in warm water to heat the material 78. It is then gripped by the user. The warm water softens the outer layer 78 to make it conformably mouldable. The grip of the user, thereafter, moulds the layer 78 as shown i.e. by moulded handle 73 in FIG. 3 to his particular grip. Setting may be hastened by dipping the moulded handle in cold water. The moulding process may be repeated several times until the best grip is achieved. Alternatively the moulding process may be repeated as the bat is used by different persons. It may be repeatedly re-moulded daily if required.

When warm water is referred to herein, it is meant that the temperature of the water is sufficient to make the material according to the invention become conformably mouldable. This temperature is usually from 50° C. to 95° C.

From the possible range of uses of the material it will be appreciated that the set hardness will not necessarily be the same for all end uses. For example, an insole (FIG. 5) will generally be harder than a table tennis bat handle.

Figure 5:
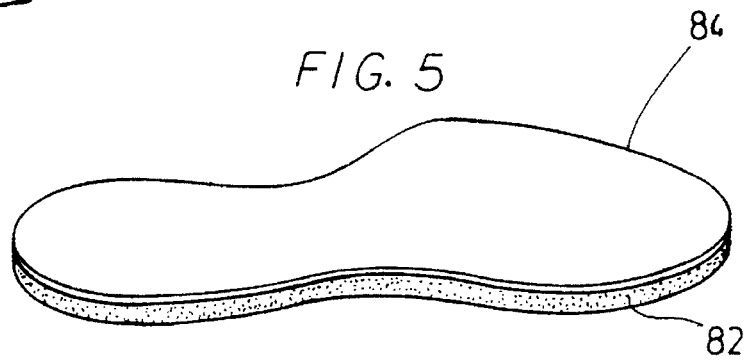

FIG. 5 shows an insole for a shoe having a lower layer 82 formed of conventional insole material such as foam rubber. The insole also includes an upper layer 84 formed of the mouldable, conformable composition of the invention. When the insole is heated to a temperature between about 50° C. and 95° C. the upper layer 84 becomes mouldable. At a temperature within this range comfortable to the user the upper layer may be moulded to fit the shape of the foot. Thereafter, at body temperature, the shape is retained. The process may be repeated several times ie. the article may be reheated and re-moulded several times, to ensure the best possible fit. Alternatively it may be desirable to move the insoles from one pair of shoes to another, and again the articles can be reheated and remoulded, even daily, as required.

Figure 4:
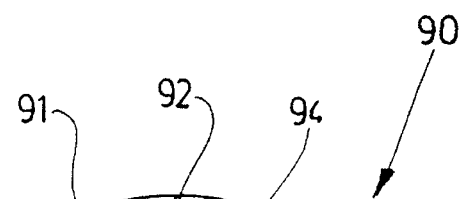
FIG. 4 shows a protective helmet according to the invention, partially in section, and, FIG. 5 shows an insole for a shoe according to the invention.

FIG. 4 shows a protective helmet 90 for example a hockey helmet, in general outline. A section of the helmet is cut away to show the outer shell 91, and foam padding 92. An upper portion of padding 92 is provided with an inwardly directed layer 94 of thermoplastic mouldable material according to the invention which is conformably mouldable between 50° C. and 95° C. Such a hockey helmet may have the layer 96 moulded to conform to the head contours of a user by heating the helmet to a temperature within the range of about 50° C. to 95° C. At a temperature comfortable to the user but within this range, the layer 96 may be moulded to the shape of the user's head. Thereafter, at body temperature the layer will retain its moulded shape. It can be repeatedly reheated and re-moulded as required.

Various materials according to the invention and their method of preparation will now be described by way of example.

EXAMPLES 1–6

Conformably re-mouldable compositions capable of repeated re-moulding were prepared as follows:

A polymer powder mixture was prepared comprising 99 parts by weight of solid polyethyl methacrylate and one part by weight benzoyl peroxide which is a polymerization initiator.

A monomer mixture was prepared according to the ingredients and proportions set out in Table I.

TABLE I

| MONOMER LIQUID | MIX 1 | MIX 2 | MIX 3 | MIX 4 | MIX 5 | MIX 6 |
|---|---|---|---|---|---|---|
| 1. Methyl methacrylate (inhibited with hydroquinone 50 ppm) | 54.5 | 27.8 | 76.75 | 63.4 | 58.95 | 72.3 |
| 2. Butyl methacrylate | 5 | 8 | 2.5 | 4 | 4.5 | 3 |
| 3. Dibutyl phthalate | 22 | 35.2 | 11 | 17.6 | 19.8 | 13.2 |
| 4. Dioctyl phthalate | 18 | 28.8 | 9 | 14.4 | 16.2 | 10.8 |
| 5. Ethylene glycol dimethacrylate | 0.5 | 0.2 | 0.75 | 0.6 | 0.55 | 0.7 |

The compositions of liquid mixtures 1–6 were each mixed with the polymer powder mixture in a ratio of one part liquid mixture to two parts polymer powder mixture. Each of the resulting liquid monomer/solid polymers was held at 100° C. in boiling water for a period of 30 minutes to polymerize the monomer, and resulted in six thermoplastic polymer mix compositions 1+6. Each polymer mix composition was used to mould various articles at between 50° C. to 95° C.

It will be appreciated that the hardness or softness of the resulting product is dependent upon the proportion of methacrylate monomer used in the liquid monomer mixture. It is possible to vary the ratio of liquid monomer to polymer powder within a range of, for example, 1:1 to 1:3 by weight.

Methyl methacrylate in the monomer liquid is mixed with butyl methacrylate as shown in the Table.

Other polymerization inhibitors are, of course possible but should only be present in an amount to inhibit premature polymerization prior to mixing with polymer. Many other variations and modifications are possible within the scope of the invention.

In accordance with the formulations of the invention described the re-moulding operation maybe carried out if desired on a daily basis repeatedly.

The foregoing is a description of a preferred embodiment of the invention which is given here by way of example only. The invention is not to be taken as limited to any of the specific features as described, but comprehends all such variations thereof as come within the scope of the appended claims.

What is claimed is:

1. A re-mouldable settable personal hand conforming article forming part of a personally portable hand held device, said article being located on the exterior of said device for contact with the person and being capable of daily repeated reheating and remoulding for repeated daily customization to the shape of a hand of the person by a user, and comprising, a thermoplastic polymerised composition which is set hard at ambient temperatures up to about 37° C. and which may be repeatedly rendered conformably mouldable at elevated temperatures of between about 50° C. and 95° C. to be repeatedly re-moulded during daily use to conform to the hand of the person, and which remains hard when in contact with the person and cooled to body temperature, said thermoplastic polymerised composition in turn comprising;

a liquid mixture of,
 a first predetermined quantity of liquid methyl methacrylate monomer in an amount of about 27 to 76 parts per hundred of said liquid mixture;
 a second predetermined quantity of liquid butyl methacrylate monomer in an amount of about 2.5 to 8 parts per hundred of said liquid mixture, and,
 a third predetermined quantity of a plasticizer mixture, in an amount of about 20 to 63 parts per hundred of said liquid mixture; and,
a powdered polyethyl methacrylate polymer together with a polymerisation initiator, mixed with said liquid mixture in a ratio of about from one part to about two parts by weight of powdered polyethyl methacrylate polymer, to about one part by weight of said liquid mixture, said powdered polyethyl methacrylate polymer being at least substantially set at temperatures below about 95° C., said liquid mixture and said powdered polyethyl methacrylate polymer in said composition being polymerised, whereby said polymerised composition remains set after polymerisation at temperatures in the region up to about 37° C. and which may be repeatedly rendered substantially manually re-mouldable in daily use at temperatures between about 50° C. and 95° C.

2. A re-mouldable settable personal hand conforming article as claimed in claim 1, wherein said plasticizer mixture comprises a mixture of dibutyl phthalate and dioctyl phthalate.

3. A re-mouldable, personal hand conforming article as claimed in claim 1 in which said liquid monomer mixture and said powdered polyethyl methacrylate polymer are present in a ratio of about 1:1.5 by weight respectively.

4. A re-mouldable, settable personal hand conforming article as claimed in claim 1 in which said liquid mixture includes ethylene glycol dimethacrylate as a cross-linking agent.

5. A re-mouldable, settable personal hand conforming article as claimed in claim 1 wherein said article is a handpiece adapted to be held in the hand and comprising a base having an approximate generally desired handle shape and a cover portion for said base comprising a thermoplastic composition which is set at temperatures up to about 37° C. and which is conformably repeatedly re-mouldable at temperatures in the region of between about 50° C. and 95° C.

6. A re-mouldable settable personal head conforming article forming part of a personally portable head protection device wherein said device is a protective helmet having an outer shell, and, an inner layer in said shell, formed of repeatedly re-mouldable, settable material comprising a thermoplastic composition which is set at temperatures up to about 37° C. and which is conformably re-mouldable at temperatures in the region of between about 50° C. and 95° C., said article being located on the interior of said device for contact with the head of the person and being capable of daily repeated reheating and remoulding for repeated daily customization to the shape of the head of the person by a user, and comprising, a thermoplastic polymerised composition which is set hard at ambient temperatures up to about 37° C. and which may be repeatedly rendered conformably mouldable at elevated temperatures of between about 50° C. and 95° C. to be repeatedly re-moulded during daily use to conform to the head of the person, and which remains hard when in contact with the person and cooled to body temperature, said thermoplastic polymerised composition in turn comprising;

a liquid mixture of,
- a first predetermined quantity of liquid methyl methacrylate monomer in an amount of about 27 to 76 parts per hundred of said liquid mixture;
- a second predetermined quantity of liquid butyl methacrylate monomer in an amount of about 2.5 to 8 parts per hundred of said liquid mixture, and,
- a third predetermined quantity of a plasticizer mixture, in an amount of about 20 to 63 parts per hundred of said liquid mixture; and, a powdered polyethyl methacrylate polymer together with a polymerisation initiator, mixed with said liquid mixture in a ratio of about from one part to about two parts by weight of powdered polyethyl methacrylate polymer, to about one part by weight of said liquid mixture, said powdered polyethyl methacrylate polymer being at least substantially set at temperatures below about 95° C., said liquid mixture and said powdered polyethyl methacrylate polymer in said composition being polymerised, whereby said polymerised composition remains set after polymerisation at temperatures in the region up to about 37° C. and which may be repeatedly rendered substantially manually re-mouldable in daily use at temperatures between about 50° C. and 95° C.

7. A re-mouldable settable personal foot conforming article forming part of a personally foot supporting device, wherein said article is an insole for a shoe and having a base having an approximate generally desired insole shape and an upper layer secured to said base, formed of a thermoplastic composition which is set at temperatures up to about 37° C. and which is conformably repeatedly re-mouldable at temperatures in the region of between about 50° C. and 95° C. said article being located on the exterior of said device for contact with the foot of the person and being capable of daily repeated reheating and remoulding for repeated daily customization to the shape of the foot of the person by a user, and comprising, a thermoplastic polymerised composition which is set hard at ambient temperatures up to about 37° C. and which may be repeatedly rendered conformably mouldable at elevated temperatures of between about 50° C. and 95° C. to be repeatedly re-moulded during daily use to conform to the foot of the person, and which remains hard when in contact with the person and cooled to body temperature, said thermoplastic polymerised composition in turn comprising;

a liquid mixture of,
- a first predetermined quantity of liquid methyl methacrylate monomer in an amount of about 27 to 76 parts per hundred of said liquid mixture;
- a second predetermined quantity of liquid butyl methacrylate monomer in an amount of about 2.5 to 8 parts per hundred of said liquid mixture, and,
- a third predetermined quantity of a plasticizer mixture, in an amount of about 20 to 63 parts per hundred of said liquid mixture; and, a powdered polyethyl methacrylate polymer together with a polymerisation initiator, mixed with said liquid mixture in a ratio of about from one part to about two parts by weight of powdered polyethyl methacrylate polymer, to about one part by weight of said liquid mixture, said powdered polyethyl methacrylate polymer being at least substantially set at temperatures below about 95° C., said liquid mixture and said powdered polyethyl methacrylate polymer in said composition being polymerised, whereby said polymerised composition remains set after polymerisation at temperatures in the region up to about 37° C. and which may be repeatedly rendered substantially manually re-mouldable in daily use at temperatures between about 50° C. and 95° C.

\* \* \* \* \*